United States Patent
Ikeda

(10) Patent No.: US 9,420,787 B2
(45) Date of Patent: Aug. 23, 2016

(54) METHOD FOR CONTROLLING NOXIOUS ORGANISMS

(71) Applicant: SUMITOMO CHEMICAL COMPANY, LIMITED, Tokyo (JP)

(72) Inventor: Hajime Ikeda, Kasai (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 4 days.

(21) Appl. No.: 14/693,512

(22) Filed: Apr. 22, 2015

(65) Prior Publication Data

US 2015/0223455 A1    Aug. 13, 2015

Related U.S. Application Data

(62) Division of application No. 13/910,711, filed on Jun. 5, 2013, now Pat. No. 9,040,456.

(30) Foreign Application Priority Data

Sep. 10, 2012  (JP) .................................. 2012-198157

(51) Int. Cl.

| A01N 43/78 | (2006.01) |
|---|---|
| A01N 41/06 | (2006.01) |
| A01N 43/653 | (2006.01) |
| A01N 43/84 | (2006.01) |
| A01N 43/54 | (2006.01) |
| A01N 33/22 | (2006.01) |

(52) U.S. Cl.
CPC ............... *A01N 41/06* (2013.01); *A01N 33/22* (2013.01); *A01N 43/54* (2013.01); *A01N 43/653* (2013.01); *A01N 43/78* (2013.01); *A01N 43/84* (2013.01)

(58) Field of Classification Search
CPC .............................. A01N 41/06; A01N 43/78
See application file for complete search history.

(56) References Cited

U.S. PATENT DOCUMENTS

| 4,285,723 A * | 8/1981 | Cartwright ............. A01N 41/06 504/311 |
|---|---|---|
| 2009/0143447 A1 | 6/2009 | Arthur et al. |
| 2010/0317520 A1 | 12/2010 | Ikeda et al. |

FOREIGN PATENT DOCUMENTS

WO   WO 02/066471 A1   8/2002

OTHER PUBLICATIONS

Askew, S.D. et al., "Cotton (*Gossypium hirsutum*) and weed response to flumioxazin applied preplant and postemergence directed," Weed Technology, vol. 16, pp. 184-90 (2002).
Meister et al., "The Building Blocks for Global Food Security", MEISTERPRO Crop Protection Handbook, vol. 98, pp. 6-7, 438-439, 442-443, 452-453, 566-567, 634-635 and 654-655, ISBN: 1-892829-25-8.
Valor label, Valent U.S.A. Corp. (2010).
Wood, "Compendium of Pesticide Common Names", published online: http://www.alanwood.net/pesticides/, (retrieved Jul. 7, 2014).

\* cited by examiner

*Primary Examiner* — John Pak
(74) *Attorney, Agent, or Firm* — Birch, Stewart, Kolasch & Birch, LLP

(57) ABSTRACT

To provide a method which exerts excellent controlling effects on noxious organisms in a field of soybean, corn or cotton.

A method for controlling noxious organisms in a field of soybean, corn or cotton, wherein at least one PPO inhibitor compound selected from the group consisting of flumioxazin, sulfentrazone, saflufenacil, oxyfluorfen, fomesafen-sodium, and a compound represented by formula (I):

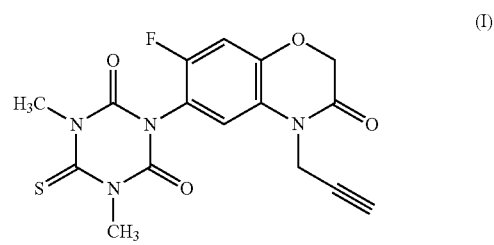

is applied to the field before, at or after sowing a soybean, corn or cotton seed treated with ethaboxam.

8 Claims, No Drawings

METHOD FOR CONTROLLING NOXIOUS ORGANISMS

CROSS-REFERENCE TO RELATED APPLICATIONS

This application is a Divisional of co-pending application Ser. No. 13/910,711 filed on Jun. 5, 2013, which claims priority under 35 U.S.C. §119(a) to Patent Application No. 2012-198157 filed in Japan on Sep. 10, 2012. All of the above applications are hereby expressly incorporated by reference into the present application.

BACKGROUND OF THE INVENTION

1. Field of the Invention

The present invention relates to a method for controlling noxious organisms, namely plant pathogens and/or weeds.

2. Description of the Related Art

Ethaboxam is known as an active ingredient of fungicides. In addition, a PPO inhibitor compound is known as an active ingredient of herbicides.

PRIOR ART LITERATURES

Patent Literature

Patent Literature 1: WO 02/066471

Non-Patent Literatures

Non-patent Literature 1: Crop Protection Handbook, vol. 98 (2012) Meister Publishing Company, ISBN: 1-892829-25-8)

Non-patent Literature 2: Compendium of Pesticide Common Names (http://www.alanwood.net/pesticides/)

The present invention provides a method which exerts excellent controlling effects on noxious organisms in a field of soybean, corn or cotton.

SUMMARY OF THE INVENTION

The present invention is to achieve excellent controlling effects on noxious organisms occurring in a field by applying a PPO inhibitor compounds to a field of soybean, corn or cotton before, at or after sowing a soybean, corn or cotton seed treated with ethaboxam.

The present invention includes the following.

[1] A method for controlling weeds in a field of soybean, corn or cotton, wherein at least one PPO inhibitor compound selected from the group consisting of flumioxazin, sulfentrazone, saflufenacil, oxyfluorfen, fomesafen-sodium, and
a compound represented by formula (I):

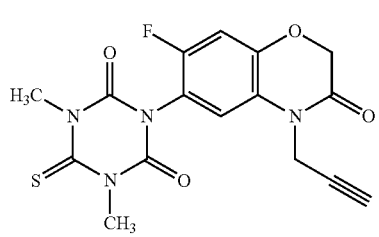

is applied before, at or after sowing a soybean, corn or cotton seed treated with ethaboxam.

[2] A method for controlling noxious organisms in a field of soybean, corn or cotton, which comprises the steps of treating a soybean, corn or cotton seed with ethaboxam, and
applying at least one PPO inhibitor compound selected from the group consisting of flumioxazin, sulfentrazone, saflufenacil, oxyfluorfen, fomesafen-sodium, and a compound represented by formula (I):

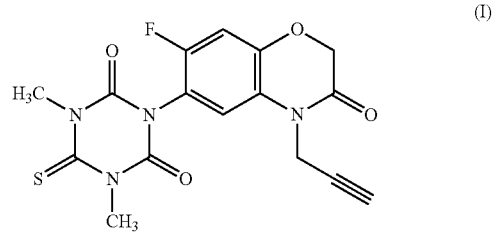 [SMILES: C#CCN1C(=O)COc2cc(F)c(-n3c(=O)n(C)c(=S)n(C)c3=O)cc21]

before, at or after sowing the soybean, corn or cotton seed treated with ethaboxam

[3] The control method according to [1] or [2], wherein the PPO inhibitor compound is flumioxazin.

[4] The control method according to [1] or [2], comprising the step of applying the PPO inhibitor compound to the field before sowing the soybean, corn or cotton seed.

[5] The control method according to [1] or [2], comprising the step of applying the PPO inhibitor compound to the field at sowing the soybean, corn or cotton seed.

[6] The control method according to [1] or [2], comprising the step of applying the PPO inhibitor compound to the field after sowing the soybean, corn or cotton seed.

[7] The control method according to [2], wherein the noxious organisms are weeds and/or plant pathogens.

[8] The control method according to [2], wherein the noxious organisms are weeds.

According to the method for controlling noxious organisms of the present invention, noxious organisms in a field of soybean, corn or cotton can be controlled.

DETAILED DESCRIPTION OF THE PREFERRED EMBODIMENTS

The method for controlling noxious organisms of the present invention comprises the steps of
(1) treating a soybean, corn or cotton seed with ethaboxam, and
(2) applying at least one PPO inhibitor compound selected from the group consisting of flumioxazin, sulfentrazone, saflufenacil, oxyfluorfen, fomesafen-sodium, and
a compound represented by formula (I):

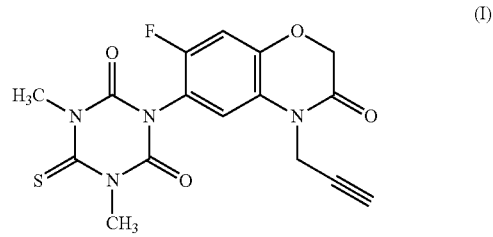 [SMILES: C#CCN1C(=O)COc2cc(F)c(-n3c(=O)n(C)c(=S)n(C)c3=O)cc21]

to the field before, at or after sowing the soybean, corn or cotton seed treated with ethaboxam.

In the present invention, the seed of soybean, corn or cotton is not limited as far as it is a variety which is generally cultivated as a crop.

Examples of a plant of such a variety include plants to which resistance to a PPO-inhibiting compound such as flumioxazin; a 4-hydroxyphenylpyruvatedioxygenase-inhibiting compound such as isoxaflutole; an acetolactate synthase (hereinafter abbreviated as ALS)—inhibiting compound such as imazethapyr or thifensulfuron methyl; a 5-enolpyruvylshikimate-3-phosphate synthase—inhibiting compound such as glyphosate; a glutamine synthase—inhibiting compound such as glufosinate; an auxin-type herbicide such as 2, 4-D or dicamba; or bromoxynil has been imparted by a classical breeding method or a genetic engineering technique.

Examples of a crop to which resistance has been imparted by a classical breeding method include corn resistant to an imidazolinone type ALS—inhibiting herbicide such as imazethapyr, and this has already been commercially available under a trade name of Clearfield (registered trademark). Examples of such a crop also include STS soybean which is resistant to a sulfonylurea—type ALS—inhibiting herbicide such as thifensulfuron methyl. Similarly, examples of a plant to which resistance to an acetyl CoA carboxylase—inhibiting compound such as trione oxime-type or aryloxyphenoxypropionic acid—type herbicide has been imparted by a classical breeding method include SR corn.

Examples of a plant to which resistance has been imparted by a genetic engineering technique include corn, soybean and cotton varieties which are resistant to glyphosate, and they have already been commercially available under trade names of RoundupReady (registered trade mark), Agrisure (registered trademark) GT, Gly-Tol (registered trademark) and the like. Similarly, there are corn, soybean and cotton varieties which are resistant to glufosinate by a genetic engineering technique, and they have already been commercially available under trade names of LibertyLink (registered trademark) and the like. There are corn and soybean varieties under the trade name of Optimum (registered trademark) GAT (registered trade mark), which are resistant to both of glyphosate and an ALS-inhibiting compound. Similarly, there are soybean varieties which are resistant to an imidazolinone—type ALS—inhibiting compound by a genetic engineering technique, and they have been developed under the name of Cultivance. Similarly, there is cotton varieties which are resistant to bromoxynil by a genetic engineering technique, and this has already been commercially available under the trade name of BXN (registered trademark).

A crop such as a soybean which is resistant to dicamba can be produced by introducing a dicamba degrading enzyme such as dicamba monooxygenase isolated from *Pseudomonas maltophilia* into a plant (Behrens et al. 2007 Science 316: 1185-1188).

By introducing a gene encoding aryloxyalkanoate dioxygenase, a crop which becomes resistant to a phenoxy acid-type herbicide such as 2,4-D, MCPA, dichlorprop or mecoprop, and an aryloxyphenoxypropionic acid-type herbicide such as quizalofop, haloxyfop, fluazifop, diclofop, fenoxaprop, metamifop, cyhalofop and clodinafop can be produced (Wright et al. 2010: Proceedings of National Academy of Science. 107 (47): 20240-20245).

The crop includes, for example, a crop which has become possible to synthesize a selective toxin known in *Bacillus* genus, using a genetic engineering technique.

Examples of the toxin which is expressed in such a genetically engineered plant include an insecticidal protein derived from *Bacillus cereus* or *Bacillus popilliae*; a δ-endotoxin such as Cry1Ab, Cry1Ac, Cry1F, Cry1Fa2, Cry2Ab, Cry3A, Cry3Bb1, Cry9C, Cry34ab and Cry35ab, derived from *Bacillus thuringiensis*; an insecticidal protein such as VIP1, VIP2, VIP3 or VIP3A; an insecticidal protein derived from nematode; a toxin produced by an animal such as a scorpion toxin, a spider toxin, a bee toxin or an insect-specific neurotoxin; a filamentous fungus toxin; plant lectin; agglutinin; a protease inhibitor such as a trypsin inhibitor, a serine protease inhibitor, patatin, cystatin, and a papain inhibitor; a ribosome inactivating protein (RIP) such as lysine, corn-RIP, abrin, luffin, saporin or bryodin; a steroid metabolism enzyme such as 3-hydroxysteroid oxidase, ecdysteroid-UDP-glycosyltransferase, and cholesterol oxidase; an ecdysone inhibitor; HMG-CoA reductase; an ion channel inhibitor such as a sodium channel inhibitor or a calcium channel inhibitor; juvenile hormone esterase; a diuretic hormone receptor; stilbene synthase; bibenzyl synthase; chitinase; glucanase; and the like.

A toxin expressed by such a genetically engineered crop includes a hybrid toxin of a δ-endotoxin protein such as Cry1Ab, Cry1Ac, Cry1F, Cry1Fa2, Cry2Ab, Cry3A, Cry3Bb1, Cry9C, Cry34Ab or Cry35Ab, and an insecticidal protein such as VIP1, VIP2, VIP3 or VIP3A, and a partially deleted toxin, and a modified toxin. The hybrid toxin can be produced by a new combination of different domains of these proteins using a genetic engineering technique. As the partially deleted toxin, Cry1Ab in which a part of an amino acid sequence has been deleted is known. In the modified toxin, one or a plurality of amino acids of a natural toxin are substituted. Examples of these toxins and recombinant plants which can synthesize these toxins are described in EP-A-0374753, WO 93/07278, WO 95/34656, EP-A-0427529, EP-A-451878, WO 03/052073 and the like. The toxins contained in these recombinant plans impart resistance to Coleoptera vermin, Diptera vermin and Lepidoptera vermin to a plant.

In addition, a genetically engineered plant containing one or a plurality of insecticidal vermin-resistant genes and expressing one or a plurality of toxins has already been known, and some of them are commercially available. Examples of these genetically engineered plants include YieldGard (registered trademark) (corn variety expressing Cry1Ab toxin), YieldGard Rootworm (registered trademark) (corn variety expressing Cry3Bb1 toxin), YieldGard Plus (registered trademark) (corn variety expressing Cry1Ab and Cry3Bb1 toxins), Herculex I (registered trademark) (corn variety expressing phosphinothricin N-acetyltransferase (PAT) for imparting resistance to a Cry1Fa2 toxin and glufosinate), NatureGard (registered trademark), AGRI-SURE (registered trademark) CB Advantage (Bt11 corn-borer (CB) trait), and Protecta (registered trademark).

In addition, genetically engineered cotton containing one or a plurality of insecticidal vermin-resistant genes and expressing one or a plurality of toxins have already been known, and some of them are commercially available. Examples of these genetically engineered cotton include BollGard (registered trademark) (cotton variety expressing Cry1Ac toxin), BollGard (registered trademark) II (cotton variety expressing Cry1Ac and Cry2Ab toxins), BollGard (registered trademark) III (cotton variety expressing Cry1Ac, Cry2Ab and VIP3A toxins), VipCot (registered trademark) (cotton variety expressing VIP3A and Cry1Ab toxins), WideStrike (registered trademark) (cotton variety expressing Cry1Ac and Cry1F toxins).

Examples of the plant used in the present invention also include plants to which resistance to an aphid has been imparted, such as soybeans into which a Rag1 (Resistance Aphid Gene 1) gene has been introduced.

In addition, the plant used in the present invention also includes those provided with the resistance to nematodes using a classical breeding method or genetic recombination technology. RNAi is exemplified as the genetic recombination technology providing nematode resistance.

The crop also includes a crop to which the ability to produce an anti-pathogenic substance having selective action has been imparted using a genetic engineering technique. As an example of the anti-pathogenic substance, a PR protein and the like are known (PRPs, EP-A-0392225). Such an anti-pathogenic substance and a genetically engineered plant producing the substance are described in EP-A-0392225, WO 95/33818, EP-A-0353191 and the like. Examples of the anti-pathogenic substance expressed in such a genetically engineered plant include an ion channel inhibitor such as a sodium channel inhibitor or a calcium channel inhibitor (KP1, KP4 and KP6 toxins, etc., which are produced by viruses, have been known); stilbene synthase; bibenzyl synthase; chitinase; glucanase; a PR protein; and an anti-pathogenic substance generated by microorganisms, such as a peptide antibiotic, an antibiotic having a hetero ring, or a protein factor associated with resistance to plant diseases (which is called a plant disease-resistant gene and is described in WO 03/000906).

The crop also includes a plant to which a useful character such as oil cake component modification or an amino acid content enhancing character has been imparted using a genetic engineering technique. Examples thereof include VISTIVE (registered trademark) (low linolenic soybean having a reduced linolenic content) and high-lysine (high-oil) corn (corn having an increased lysine or oil content).

Further, stack varieties are also included in which a plurality of the classical herbicide character or herbicide-resistant gene, insecticidal vermin-resistant gene, anti-pathogenic substance production gene, and a useful character such as oil cake component modification or amino acid content enhancing character are combined.

Ethaboxam used for seed treatment in the present invention is a known compound, and commercially available formulations and reference standards can be purchased and used.

In the step of treating a soybean, corn or cotton seed with ethaboxam in the present invention, ethaboxam is usually mixed with a solid carrier or liquid carrier, and further formulated with addition of an auxiliary agent for formulations, such as surfactants, if necessary. Preferred dosage form is an aqueous liquid suspension formulation.

Ethaboxam is applied in an amount in the range of usually 0.2 to 5000 g, preferably 0.5 to 1000 g, more preferably 1 to 1000 g, and further preferably 5 to 500 g, per 100 kg of seeds. Examples of the method for applying the active ingredient to plant seeds include a method of subjecting seeds to dust coating with a formulation containing the active ingredient, a method of immersing seeds in a formulation containing the active ingredient, a method of spraying seeds with a formulation containing the active ingredient, and a method of coating seeds with a carrier containing the active ingredient.

The present invention includes the step of applying at least one PPO inhibitor compound to the field before, at or after sowing a soybean, corn or cotton seed treated with ethaboxam.

The PPO inhibitor compound is a herbicidal active compound which inhibits protoporphyrinogen IX oxidase (EC1.3.3.4) located on a chlorophyll synthesis pathway in plant plastids, thereby causing death of the plant.

The PPO inhibitor compound in the present invention includes flumioxazin, sulfentrazone, saflufenacil, oxyfluorfen, fomesafen-sodium, and a compound represented by formula (I):

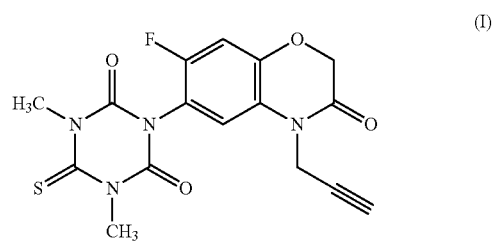 [SMILES: C#CCN1C(=O)COc2cc(F)c(-n3c(=O)n(C)c(=S)n(C)c3=O)cc21]

(hereinafter referred to as compound 1).

These PPO inhibitor compounds are all known compounds, and compound 1 is synthesized by the method described in the Patent Literature 1. As other compounds, commercially available formulations and reference standards can be purchased and used.

In the step of applying the PPO inhibitor compound to the field, the PPO inhibitor compound is usually mixed with a solid carrier or liquid carrier, and further formulated with addition of an auxiliary agent for formulations, such as surfactants, if necessary.

Examples of the step of applying the PPO inhibitor compound to the field include a method of spraying a PPO inhibitor compound on the soil in the field, and a method of spraying a PPO inhibitor compound on the weeds after their germination.

The amount of the PPO inhibitor compound used in the step of applying the PPO inhibitor compound to the field is usually 5 to 5000 g per 10000 $m^2$, preferably 10 to 1000 g per 10000 $m^2$, and more preferably 20 to 500 g per 10000 $m^2$. In the step of applying the PPO inhibitor compound to the field, an adjuvant may be mixed, and the PPO inhibitor compound may be applied.

The soybean, corn or cottonseeds treated with ethaboxam are sown in a field by the usual method. In the method for controlling noxious organisms according to the present invention, the PPO inhibitor compound may be applied before sowing a soybean, corn or cotton seed, and may be applied at sowing or after sowing a soybean, corn or cotton seed.

In the case where the PPO inhibitor compound is applied before sowing a soybean or corn seed, the PPO inhibitor compound is applied 50 days before to immediately before the sowing, preferably 30 days before to immediately before the sowing, more preferably 20 days before to immediately before the sowing, and further preferably 10 days before to immediately before the sowing.

In the case where the PPO inhibitor compound is applied after sowing a soybean or corn seed, the PPO inhibitor compound is applied preferably immediately after to 50 days after the sowing, and more preferably immediately after to 3 days after the sowing. Examples of concrete application timing in the application of the PPO inhibitor compound after sowing a soybean seed include the time from pre-emergence of soybean to flowering time. The time from pre-emergence of soybean to flowering time is preferably the time from pre-emergence of soybean to a stage of 6 compound leaves, and further preferably the time from pre-emergence of soybean to a stage of 3 compound leaves. Concrete application timing in the application of the PPO inhibitor compound after sowing a corn seed includes the time from pre-emergence of corn to 12 leaf stage, preferably the time from pre-emergence of corn to 8 leaf stage, and further preferably the time from pre-emergence of corn to 6 leaf stage. The leaf age of corn is determined by the leaf collar method.

In the case where the PPO inhibitor compound is applied before sowing a cotton seed, the PPO inhibitor compound is applied 50 days before to immediately before the sowing, preferably 30 days before to immediately before the sowing, and further preferably 20 days before to immediately before the sowing.

In the case where the PPO inhibitor compound is applied after sowing a cotton seed, the PPO inhibitor compound is applied immediately after to 70 days after the sowing and applied preferably 30 days after the sowing to 50 days after the sowing. Examples of concrete application timing in the application of the PPO inhibitor compound after sowing a cotton seed include the time from pre-emergence of cotton to flowering time. Preferably, the application timing is the time from the onset of lignification of the stem base of cotton to the stage in which the lignification part is 20 cm from the base.

According to the method for controlling noxious organisms of the present invention, noxious organisms such as plant pathogens and/or weeds in a field of soybean, corn or cotton can be controlled without causing significant phytotoxicity on crops in practical use.

Examples of the plant pathogens include the followings. *Phytophtora* spp. (*Phytophthora sojae, Phytophthora nicotianae* var. nicotianae, *Phytophthora infestans, Phytophthora erythroseptica*, and the like), *Pythium* spp. (*Pythium debaryanum, Pythium sylvaticum, Pythium graminicola, Pythium irregulare, Pythium ultimum*, and the like).

Examples of the weed include the followings:
Urticaceae weeds: *Urtica urens*
Polygonaceae weeds: *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius, Rumex acetosa*
Portulacaceae weeds: *Portulaca oleracea*
Caryophyllaceae weeds: *Stellaria media, Cerastium holosteoides, Cerastium glomeratum, Spergula arvensis, Silene gallica*
Aizoaceae weeds: *Mollugo verticillata*
Chenopodiaceae weeds: *Chenopodium album, Chenopodium ambrosioides, Kochia scoparia, Salsola kali, Atriplex* spp.
Amaranthaceae weeds: *Amaranthus retroflexus, Amaranthus viridis, Amaranthus lividus, Amaranthus spinosus, Amaranthus hybridus, Amaranthus palmeri, Amaranthus rudis, Amaranthus patulus, Amaranthus tuberculatos, Amaranthus blitoides, Amaranthus deflexus, Amaranthus quitensis, Alternanthera philoxeroides, Alternanthera sessilis, Alternanthera tenella*
Papaveraceae weeds: *Papaver rhoeas, Argemone mexicana*
Brassicaceae weeds: *Raphanus raphanistrum, Raphanus sativus, Sinapis arvensis, Capsella bursa-pastoris, Brassica juncea, Brassica campestris, Descurainia pinnata, Rorippa islandica, Rorippasylvestris, Thlaspiarvense, Myagrumrugosum, Lepidium virginicum, Coronopus didymus*
Capparaceae weeds: *Cleome affinis*
Fabaceae weeds: *Aeschynomene indica, Aeschynomene rudis, Sesbania exaltata, Cassia obtusifolia, Cassia occidentalis, Desmodium tortuosum, Desmodium adscendens, Trifolium repens, Pueraria lobata, Vicia angustifolia, Indigofera hirsuta, Indigofera truxillensis, Vigna sinensis*
Oxalidaceae weeds: *Oxalis corniculata, Oxalis strica, Oxalis oxyptera*
Geraniaceae weeds: *Geranium carolinense, Erodium cicutarium*
Euphorbiaceae weeds: *Euphorbia helioscopia, Euphorbia maculata, Euphorbia humistrata, Euphorbia esula, Euphorbia heterophylla, Euphorbia brasiliensis, Acalypha australis, Croton glandulosus, Croton lobatus, Phyllanthus corcovadensis, Ricinus communis*
Malvaceae weeds: *Abutilon theophrasti, Sida rhombifolia, Sida cordifolia, Sida spinosa, Sida glaziovii, Sida santaremnensis, Hibiscus trionum, Anoda cristata, Malvastrum coromandelianum*
Sterculiaceae weeds: *Waltheria indica*
Violaceae weeds: *Viola arvensis, Viola tricolor*
Cucurbitaceae weeds: *Sicyos angulatus, Echinocystis lobata, Momordica charantia*
Lythraceae weeds: *Lythrum salicaria*
Apiaceae weeds: *Hydrocotyle sibthorpioides*
Sapindaceae weeds: *Cardiospermum halicacabum*
Primulaceae weeds: *Anagallis arvensis*
Asclepiadaceae weeds: *Asclepias syriaca, Ampelamus albidus*
Rubiaceae weeds: *Galium aparine, Galium spurium* var. echinospermon, *Spermacoce latifolia, Richardia brasiliensis, Borreria alata*
Convolvulaceae weeds: *Ipomoea nil, Ipomoea hederacea, Ipomoea purpurea, Ipomoea hederacea* var. integriuscula, *Ipomoea lacunosa, Ipomoea triloba, Ipomoea acuminata, Ipomoea hederifolia, Ipomoea coccinea, Ipomoea quamoclit, Ipomoea grandifolia, Ipomoea aristolochiafolia, Ipomoea cairica, Convolvulus arvensis, Calystegia hederacea, Calystegia japonica, Merremia hedeacea, Merremia aegyptia, Merremia cissoides, Jacquemontia tamnifolia*
Boraginaceae weeds: *Myosotis arvensis*
Lamiaceae weeds: *Lamium purpureum, Lamium amplexicaule, Leonotis nepetaefolia, Hyptis suaveolens, Hyptis lophanta, Leonurus sibiricus, Stachys arvensis*
Solanaceae weeds: *Datura stramonium, Solanum nigrum, Solanum americanum, Solanum ptycanthum, Solanum sarrachoides, Solanum rostratum, Solanum aculeatissimum, Solanum sisymbriifolium, Solanum carolinense, Physalis angulata, Physalis subglabrata, Nicandra physaloides*
Scrophulariaceae weeds: *Veronica hederaefolia, Veronica persica, Veronica arvensis*
Plantaginaceae weeds: *Plantago asiatica*
Asteraceae weeds: *Xanthium pensylvanicum, Xanthium occidentale, Helianthus annuus, Matricaria chamomilla, Matricaria perforata, Chrysanthemum segetum, Matricaria matricarioides, Artemisia princeps, Artemisia vulgaris, Artemisia verlotorum, Solidago altissima, Taraxacum officinale, Galinsoga ciliata, Galinsoga parviflora, Senecio vulgaris, Senecio brasiliensis, Senecio grisebachii, Conyza bonariensis, Conyza canadensis, Ambrosia artemisiaefolia, Ambrosia trifida, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampodium perfoliatum, Emilia sonchifolia, Tagetes minuta, Blainvillea*

*latifolia, Tridax procumbens, Porophyllum ruderale, Acanthospermum australe, Acanthospermum hispidum, Cardiospermum halicacabum, Ageratum conyzoides, Eupatorium perfoliatum, Eclipta alba, Erechtites hieracifolia, Gamochaeta spicata, Gnaphalium spicatum, Jaegeria hirta, Parthenium hysterophorus, Siegesbeckia orientalis, Soliva sessilis*

Liliaceae weeds: *Allium canadense, Allium vineale*

Commelinaceae weeds: *Commelina communis, Commelina bengharensis, Commelina erecta*

Poaceae weeds: *Echinochloa crus-galli, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Alospecurus aequalis, Alopecurus myosuroides, Avena fatua, Sorghum halepense, Sorghum vulgare, Agropyron repens, Lolium multiflorum, Lolium perenne, Lolium rigidum, Bromus secalinus, Bromus tectorum, Hordeum jubatum, Aegilops cylindrica, Phalaris arundinacea, Phalaris minor, Apera spicaventi, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Eragrostis pilosa, Rhynchelitrum repens, Dactyloctenium aegyptium, Ischaemum rugosum, Oryza sativa, Paspalum notatum, Paspalum maritimum, Pennisetum clandestinum, Pennisetum setosum, Rottboellia cochinchinensis*

Cyperaceae weeds: *Cyperus microiria, Cyperus iria, Cyperus odoratus, Cyperus rotundus, Cyperus esculentus, Kyllinga gracillima*

Equisetaceae weeds: *Equisetum arvense, Equisetum palustre,* and the like.

In the method for controlling pests of the present invention, one or more other pesticides can be used together or separately with ethaboxam and the PPO-inhibiting compound of the present invention. Examples of other pesticide include insecticides, miticides, nematicides, fungicides, herbicides, plant growth regulators, and safeners.

Examples of the other agrochemicals include the following:

Herbicide: dicamba and a salt thereof (diglycolamine salt, dimethylammonium salt, isopropylammonium salt, potassium salt, sodium salt, choline salt), 2,4-D and a salt or ester thereof (butotyl ester, dimethylammonium salt, diolamine salt, ethylhexyl ester, isooctyl ester, isopropylammonium salt, sodium salt, triisopropanolamine salt, choline salt), 2,4-DB and a salt or ester thereof (dimethylammonium salt, isooctyl ester, choline salt), MCPA and a salt or ester thereof (dimethylammonium salt, 2-ethylhexyl ester, isooctyl ester, sodium salt, choline salt), MOPE, mecoprop and a salt or ester thereof (dimethylammonium salt, diolamine salt, ethadyl ester, 2-ethylhexyl ester, isooctyl ester, methyl ester, potassium salt, sodium salt, trolamine salt, choline salt), mecoprop-P and a salt or ester thereof (dimethylammonium salt, 2-ethylhexyl ester, isobutyl salt, potassium salt, choline salt), dichlorprop and a salt or ester thereof (butotyl ester, dimethylammonium salt, 2-ethylhexyl ester, isooctyl ester, methyl ester, potassium salt, sodium salt, choline salt), dichlorprop-P, dichlorprop-P-dimethylammonium, bromoxynil, bromoxynil-octanoate, dichlobenil, ioxynil, ioxynil-octanoate, di-allate, butylate, tri-allate, phenmedipham, chlorpropham, asulam, phenisopham, benthiocarb, molinate, esprocarb, pyributicarb, prosulfocarb, orbencarb, EPTC, dimepiperate, swep, propachlor, metazachlor, alachlor, acetochlor, metolachlor, S-metolachlor, butachlor, pretilachlor, thenylchlor, aminocyclopyrachlor, aminocyclopyrachlor-methyl, aminocyclopyrachlor-potassium, trifluralin, pendimethalin, ethalfluralin, benfluralin, prodiamine, simazine, atrazine, propazine, cyanazine, ametryn, simetryn, dimethametryn, prometryn, indaziflam, triaziflam, metribuzin, hexazinone, isoxaben, diflufenican, diuron, linuron, fluometuron, difenoxuron, methyl-daimuron, isoproturon, isouron, tebuthiuron, benzthiazuron, methabenzthiazuron, propanil, mefenacet, clomeprop, naproanilide, bromobutide, daimuron, cumyluron, diflufenzopyr, etobenzanid, bentazon, tridiphane, indanofan, amitrole, fenchlorazole, clomazone, maleic hydrazide, pyridate, chloridazon, norflurazon, bromacil, terbacil, oxaziclomefone, cinmethylin, benfuresate, cafenstrole, pyrithiobac, pyrithiobac-sodium, pyriminobac, pyriminobac-methyl, bispyribac, bispyribac-sodium, pyribenzoxim, pyrimisulfan, pyriftalid, fentrazamide, dimethenamid, dimethenamid-P, ACN, bennzobicyclon, dithiopyr, triclopyr and a salt or ester thereof (butotyl ester, triethylammonium salt), fluroxypyr, fluroxypyr-meptyl, thiazopyr, aminopyralid and a salt thereof (potassium salt, triisopropanolammonium salt, choline salt), clopyralid and a salt thereof (olamine salt, potassium salt, triethylammonium salt, choline salt), picloram and a salt thereof (potassium salt, triisopropanolammonium salt, choline salt), dalapon, chlorthiamid, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, mesosulfuron, mesosulfuron-methyl, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron, trifloxysulfuron-sodium, trifloxysulfuron, chlorsulfuron, cinosulfuron, ethametsulfuron, ethametsulfuron-methyl, iodosulfuron, iodosulfuron-methyl-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, picolinafen, beflubutamid, mesotrione, sulcotrione, tefuryltrione, tembotrione, isoxachlortole, isoxaflutole, benzofenap, pyrasulfotole, pyrazolynate, pyrazoxyfen, topramezone, flupoxam, amicarbazone, bencarbazone, flucarbazone, flucarbazone-sodium, ipfencarbazone, propoxycarbazone, propoxycarbazone-sodium, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium, imazapic, imazapic-ammonium, imazapyr, imazapyr-ammonium, imazaquin, imazaquin-ammonium, imazethapyr, imazethapyr-ammonium, clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, pinoxaden, pyroxasulfone, glyphosate, glyphosate-isopropylamine, glyphosate-trimethylsulfonium, glyphosate-ammonium, glyphosate-diammonium, glyphosate-sodium, glyphosate-potassium, glyphosate-guanidine, glufosinate, glufosinate-ammonium, glufosinate-P, glufosinate-P-sodium, bialafos, anilofos, bensulide, butamifos, paraquat, paraquat-dichloride, diquat and diquat-dibromide Plant growth regulating agents: hymexazol, paclobutrazol, uniconazole, uniconazole-P, inabenfide, prohexadione-calcium, 1-methylcyclopropene, trinexapac and gibberellins.

Safeners: benoxacor, cloquintocet, cloquintocet-mexyl, cyometrinil, cyprosulfamide, dichlormid, dicyclonon, dietholate, fenchlorazole, fenchlorazole-ethyl, fenclorim, flurazole, fluxofenim, furilazole, isoxadifen, isoxadifen-ethyl, mefenpyr, mefenpyr-diethyl, mephenate, naphthalic anhydride and oxabetrinil.

EXAMPLES

Hereinbelow, the present invention will be described by way of Examples, but the present invention is not limited to these Examples. Here, hectare (ha) in the following descriptions means 10000 m².

First, evaluation criteria for a plant pathogen controlling effect, a herbicidal effect described in the following examples are shown.

[Plant Pathogen Controlling Effect]

The evaluation of the plant pathogen controlling effect is classified into 0 to 100, in which the numeral "0" indicates no or little difference in the symptom by plant pathogen as compared with the untreated weeds at the time of the investigation, and the numeral "100" indicates that the symptom by plant pathogen is completely unobserved or hardly observed.

[Herbicidal Effect]

The evaluation of the herbicidal effect is classified into 0 to 100, in which the numeral "0" indicates no or little difference in the state of germination or growth of test weeds as compared with the untreated weeds at the time of the investigation, and the numeral "100" indicates the complete death of the test plants or the complete suppression of their germination or growth.

Example 1

In a plastic cup of 100 mm in inside diameter and 40 mm in height, 10.5 mg of an ethaboxam suspension (a suspension containing 34.6% of ethaboxam, manufactured by Valent USA Corp.) and 40 soybean seeds were placed. The plastic cup was shaken by the hand so that the ethaboxam suspension was attached to the soybean seeds. The weight of 40 soybean seeds was 12.1 g, and the amount of ethaboxam by the above treatment was calculated as 30 g per 100 kg of the soybean seeds.

In the same manner, 104.9 mg of the ethaboxam suspension was attached to 40 soybean seeds. The weight of 40 soybean seeds was 12.1 g, and the amount of ethaboxam by the above treatment was calculated as 300 g per 100 kg of the soybean seeds.

A soil was packed in a plastic pot of 120 mm in inside diameter×80 mm in height. The above treated soybean seeds were sown in this pot at a rate of two seeds per pot, and the seeds of ivyleaf morningglory were sown at a rate of four seeds per pot. On the day of sowing the soybean seeds and after sowing the soybean seeds, an aqueous diluted solution (113 mg of active ingredient/L or 225 mg of active ingredient/L) of a flumioxazin granular wettable powder (a granular wettable powder containing 51% of flumioxazin, trade name: Valor SX, manufactured by Valent USA), an aqueous diluted solution (226 mg of active ingredient/L or 1130 mg of active ingredient/L) of a sulfentrazone granular wettable powder (a granular wettable powder containing 75% of sulfentrazone, trade name: Cover, manufactured by DuPont), or an aqueous diluted solution (113 mg/L or 226 mg/L) of saflufenacil was uniformly sprayed on the soil surface with a sprayer so as to apply the amount described in Tables 1 to 3. The aqueous diluted solution of saflufenacil was prepared by dissolving a predetermined amount of saflufenacil in acetone containing 2% (w/v) of Tween 20, and diluting this solution with water so as to have an acetone concentration of 10% by volume.

On day 7 after sowing the seeds of soybean and ivyleaf morningglory, the herbicidal effect was investigated. The results are shown in Tables 1 to 3.

TABLE 1

| Treatment with ethaboxam | Treatment with flumioxazin | Herbicidal effect Ivyleaf morningglory |
|---|---|---|
| None | None | 0 |
| None | 100 g/ha | 30 |
| 30 g/100 kg of seeds | None | 0 |
| 30 g/100 kg of seeds | 50 g/ha | 100 |
| 30 g/100 kg of seeds | 100 g/ha | 100 |
| 300 g/100 kg of seeds | None | 0 |
| 300 g/100 kg of seeds | 50 g/ha | 100 |
| 300 g/100 kg of seeds | 100 g/ha | 100 |

TABLE 2

| Treatment with ethaboxam | Treatment with sulfentrazone | Herbicidal effect Ivyleaf morningglory |
|---|---|---|
| None | None | 0 |
| None | 500 g/ha | 30 |
| 30 g/100 kg of seeds | None | 0 |
| 30 g/100 kg of seeds | 100 g/ha | 95 |
| 30 g/100 kg of seeds | 500 g/ha | 100 |
| 300 g/100 kg of seeds | None | 0 |
| 300 g/100 kg of seeds | 100 g/ha | 100 |
| 300 g/100 kg of seeds | 500 g/ha | 100 |

TABLE 3

| Treatment with ethaboxam | Treatment with saflufenacil | Herbicidal effect Ivyleaf morningglory |
|---|---|---|
| None | None | 0 |
| None | 100 g/ha | 50 |
| 30 g/100 kg of seeds | None | 0 |
| 30 g/100 kg of seeds | 50 g/ha | 100 |
| 30 g/100 kg of seeds | 100 g/ha | 100 |
| 300 g/100 kg of seeds | None | 0 |
| 300 g/100 kg of seeds | 50 g/ha | 100 |
| 300 g/100 kg of seeds | 100 g/ha | 100 |

Example 2

In a plastic cup of 100 mm in inside diameter and 40 mm in height, 13.4 mg of an ethaboxam suspension (a suspension containing 34.6% of ethaboxam, manufactured by Valent USA Corp.) and 40 corn seeds were placed. The plastic cup was shaken by the hand so that the ethaboxam suspension was attached to the corn seeds. The weight of 40 corn seeds was 15.5 g, and the amount of ethaboxam by the above treatment was calculated as 30 g per 100 kg of the corn seeds.

In the same manner, 138.7 mg of the ethaboxam suspension was attached to 40 corn seeds. The weight of 40 corn seeds was 16.0 g, and the amount of ethaboxam by the above treatment was calculated as 300 g per 100 kg of the corn seeds.

A soil was packed in a plastic pot of 120 mm in inside diameter×80 mm in height. The above treated corn seeds were sown in this pot at a rate of two seeds per pot, and the seeds of ivyleaf morningglory were sown at a rate of four seeds per pot. On the day of sowing the corn seeds and after sowing the corn seeds, an aqueous diluted solution (113 mg of active ingredient/L or 225 mg of active ingredient/L) of a flumioxazin granular wettable powder (a granular wettable powder containing 51% of flumioxazin, trade name: Valor SX, manufactured by Valent USA), an aqueous diluted solution (226 mg of active ingredient/L or 1130 mg of active ingredient/L) of a sulfentrazone granular wettable powder (a granular wettable powder containing 75% of sulfentrazone, trade name: Cover, manufactured by DuPont), or an aqueous diluted solution (113 mg/L or 226 mg/L) of saflufenacil was uniformly sprayed on the soil surface with a sprayer so as to apply the amount described in Tables 4 to 6. The aqueous diluted solution of saflufenacil was prepared by dissolving a predetermined amount of saflufenacil in acetone containing 2% (w/v) of Tween 20, and diluting this solution with water so as to have an acetone concentration of 10% by volume.

On day 7 after sowing the seeds of corn and ivyleaf morningglory, the herbicidal effect was investigated. The results are shown in Tables 4 to 6.

TABLE 4

| Treatment with ethaboxam | Treatment with flumioxazin | Herbicidal effect Ivyleaf morningglory |
|---|---|---|
| None | None | 0 |
| None | 100 g/ha | 30 |
| 30 g/100 kg of seeds | None | 0 |
| 30 g/100 kg of seeds | 50 g/ha | 100 |
| 30 g/100 kg of seeds | 100 g/ha | 100 |
| 300 g/100 kg of seeds | None | 0 |
| 300 g/100 kg of seeds | 50 g/ha | 100 |
| 300 g/100 kg of seeds | 100 g/ha | 100 |

TABLE 5

| Treatment with ethaboxam | Treatment with sulfentrazone | Herbicidal effect Ivyleaf morningglory |
|---|---|---|
| None | None | 0 |
| None | 100 g/ha | 30 |
| None | 500 g/ha | 70 |
| 30 g/100 kg of seeds | None | 0 |
| 30 g/100 kg of seeds | 100 g/ha | 100 |
| 30 g/100 kg of seeds | 500 g/ha | 100 |
| 300 g/100 kg of seeds | None | 0 |
| 300 g/100 kg of seeds | 100 g/ha | 100 |
| 300 g/100 kg of seeds | 500 g/ha | 100 |

TABLE 6

| Treatment with ethaboxam | Treatment with saflufenacil | Herbicidal effect Ivyleaf morningglory |
|---|---|---|
| None | None | 0 |
| None | 100 g/ha | 30 |
| 30 g/100 kg of seeds | None | 0 |
| 30 g/100 kg of seeds | 50 g/ha | 100 |
| 30 g/100 kg of seeds | 100 g/ha | 100 |
| 300 g/100 kg of seeds | None | 0 |
| 300 g/100 kg of seeds | 50 g/ha | 100 |
| 300 g/100 kg of seeds | 100 g/ha | 100 |

Example 3

In a plastic cup of 100 mm in inside diameter and 40 mm in height, 5.7 mg of an ethaboxam suspension (a suspension containing 34.6% of ethaboxam, manufactured by Valent USA Corp.) and 40 cotton seeds were placed. The plastic cup was shaken by the hand so that the ethaboxam suspension was attached to the cotton seeds. The weight of 40 cotton seeds was 6.6 g, and the amount of ethaboxam by the above treatment was calculated as 30 g per 100 kg of the cotton seeds.

In the same manner, 56.7 mg of the ethaboxam suspension was attached to 40 cotton seeds. The weight of 40 cotton seeds was 6.55 g, and the amount of ethaboxam by the above treatment was calculated as 300 g per 100 kg of the cotton seeds.

A soil was packed in a plastic pot of 120 mm in inside diameter×80 mm in height. The above cotton seeds were sown in this pot at a rate of two seeds per pot, and the seeds of ivyleaf morningglory were sown at a rate of four seeds per pot. On the day of sowing the cottonseeds and after sowing the cotton seeds, an aqueous diluted solution (113 mg of active ingredient/L or 225 mg of active ingredient/L) of a flumioxazin granular wettable powder (a granular wettable powder containing 51% of flumioxazin, trade name: Valor SX, manufactured by Valent USA), an aqueous diluted solution (226 mg of active ingredient/L or 1130 mg of active ingredient/L) of a sulfentrazone granular wettable powder (a granular wettable powder containing 75% of sulfentrazone, trade name: Cover, manufactured by DuPont), or an aqueous diluted solution (113 mg/L or 226 mg/L) of saflufenacil was uniformly sprayed on the soil surface with a sprayer so as to apply the amount described in Tables 7 to 9. The aqueous diluted solution of saflufenacil was prepared by dissolving a predetermined amount of saflufenacil in acetone containing 2% (w/v) of Tween 20, and diluting this solution with water so as to have an acetone concentration of 10% by volume.

On day 7 after sowing the seeds of cotton and ivyleaf morningglory, the herbicidal effect was investigated. The results are shown in Tables 7 to 9.

TABLE 7

| Treatment with ethaboxam | Treatment with flumioxazin | Herbicidal effect Ivyleaf morningglory |
|---|---|---|
| None | None | 0 |
| None | 100 g/ha | 30 |
| 30 g/100 kg of seeds | None | 0 |
| 30 g/100 kg of seeds | 50 g/ha | 100 |
| 30 g/100 kg of seeds | 100 g/ha | 100 |
| 300 g/100 kg of seeds | None | 0 |
| 300 g/100 kg of seeds | 50 g/ha | 99 |
| 300 g/100 kg of seeds | 100 g/ha | 100 |

TABLE 8

| Treatment with ethaboxam | Treatment with sulfentrazone | Herbicidal effect Ivyleaf morningglory |
|---|---|---|
| None | None | 0 |
| None | 500 g/ha | 40 |
| 30 g/100 kg of seeds | None | 0 |
| 30 g/100 kg of seeds | 100 g/ha | 100 |
| 30 g/100 kg of seeds | 500 g/ha | 100 |
| 300 g/100 kg of seeds | None | 0 |
| 300 g/100 kg of seeds | 100 g/ha | 100 |
| 300 g/100 kg of seeds | 500 g/ha | 100 |

TABLE 9

| Treatment with ethaboxam | Treatment with saflufenacil | Herbicidal effect Ivyleaf morningglory |
|---|---|---|
| None | None | 0 |
| None | 50 g/ha | 20 |
| None | 100 g/ha | 70 |
| 30 g/100 kg of seeds | None | 0 |
| 30 g/100 kg of seeds | 50 g/ha | 100 |
| 30 g/100 kg of seeds | 100 g/ha | 100 |
| 300 g/100 kg of seeds | None | 0 |
| 300 g/100 kg of seeds | 50 g/ha | 100 |

Example 4

In the combinations shown in Table 10, the plant pathogen controlling effect and the herbicidal effect are confirmed by the above criteria according to the following method.

A soil is packed in a pot, and weeds are sown, then a PPO inhibitor is uniformly applied to the soil surface in doses of 25, 50, 100, 200, and 400 g/ha. After 15 days, the cotton seeds to which ethaboxam is attached in doses of 3, 30, and 300 g/100 kg of seeds are sown. The pot is placed in a greenhouse. On day 15 after the sowing, the plant pathogen controlling effect and the herbicidal effect are investigated.

TABLE 10

| Combination | Seed treatment compound | PPO inhibitor |
|---|---|---|
| 1-1 | Ethaboxam | Flumioxazin |
| 1-2 | Ethaboxam | Saflufenacil |
| 1-3 | Ethaboxam | Sulfentrazone |
| 1-4 | Ethaboxam | Oxyfluorfen |
| 1-5 | Ethaboxam | Fomesafen-sodium |
| 1-6 | Ethaboxam | Compound 1 |

Example 5

In the combinations shown in Table 11, the plant pathogen controlling effect and the herbicidal effect are confirmed by the above criteria according to the following method.

Ethaboxam is attached to cotton seeds in doses of 3, 30, and 300 g/100 kg of seeds. Next, the seeds are sown in a farm field. On 30 days after the sowing, a PPO inhibitor is applied as a post-directed application in doses of 25, 50, 100, 200, and 400 g/ha, in the state that the main stem of cotton is lignified in 15 cm from the ground. On day 28 after application, the plant pathogen controlling effect and the herbicidal effect are investigated.

TABLE 11

| Combination | Seed treatment compound | PPO inhibitor |
|---|---|---|
| 2-1 | Ethaboxam | Flumioxazin |
| 2-2 | Ethaboxam | Saflufenacil |
| 2-3 | Ethaboxam | Sulfentrazone |
| 2-4 | Ethaboxam | Oxyfluorfen |
| 2-5 | Ethaboxam | Fomesafen-sodium |
| 2-6 | Ethaboxam | Compound 1 |

Example 6

In the combinations shown in Table 12, the plant pathogen controlling effect and the herbicidal effect are confirmed by the above criteria according to the following method.

A soil is packed in a pot, and weeds are sown, then a PPO inhibitor is uniformly applied to the soil surface in doses of 25, 50, 100, 200, and 400 g/ha. After 7 days, the soybean seeds to which ethaboxam is attached in doses of 3, 30, and 300 g/100 kg of seeds are sown. The pot is placed in a greenhouse. On day 15 after the sowing, the plant pathogen controlling effect and the herbicidal effect are investigated.

TABLE 12

| Combination | Seed treatment compound | PPO inhibitor |
|---|---|---|
| 3-1 | Ethaboxam | Flumioxazin |
| 3-2 | Ethaboxam | Saflufenacil |
| 3-3 | Ethaboxam | Sulfentrazone |
| 3-4 | Ethaboxam | Oxyfluorfen |
| 3-5 | Ethaboxam | Fomesafen-sodium |
| 3-6 | Ethaboxam | Compound 1 |

Example 7

In the combinations shown in Table 13, the plant pathogen controlling effect and the herbicidal effect are confirmed by the above criteria according to the following method.

Ethaboxam is attached to the soybean seeds in doses of 3, 30, and 300 g/100 kg of seeds. Next, a soil is packed in a pot, and the seeds and seeds of the weeds are sown. At the same time as sowing, the PPO inhibitor is uniformly applied to the soil surface in doses of 25, 50, 100, 200, and 400 g/ha. The pot is placed in a greenhouse. On day 15 after the sowing, the plant pathogen controlling effect and the herbicidal effect are investigated.

TABLE 13

| Combination | Seed treatment compound | PPO inhibitor |
|---|---|---|
| 4-1 | Ethaboxam | Flumioxazin |
| 4-2 | Ethaboxam | Saflufenacil |
| 4-3 | Ethaboxam | Sulfentrazone |
| 4-4 | Ethaboxam | Oxyfluorfen |
| 4-5 | Ethaboxam | Fomesafen-sodium |
| 4-6 | Ethaboxam | Compound 1 |

Example 8

In the combinations shown in Table 14, the plant pathogen controlling effect and the herbicidal effect are confirmed by the above criteria according to the following method.

Ethaboxam is attached to the soybean seeds in doses of 3, 30, and 300 g/100 kg of seeds. Next, a soil is packed in a pot, and the seeds and seeds of the weeds are sown. On the day of sowing, the PPO inhibitor is uniformly applied to the soil surface in doses of 25, 50, 100, 200, and 400 g/ha. The pot is placed in a greenhouse. On day 15 after the sowing, the plant pathogen controlling effect and the herbicidal effect are investigated.

TABLE 14

| Combination | Seed treatment compound | PPO inhibitor |
|---|---|---|
| 5-1 | Ethaboxam | Flumioxazin |
| 5-2 | Ethaboxam | Saflufenacil |
| 5-3 | Ethaboxam | Sulfentrazone |
| 5-4 | Ethaboxam | Oxyfluorfen |
| 5-5 | Ethaboxam | Fomesafen-sodium |
| 5-6 | Ethaboxam | Compound 1 |

Example 9

In the combinations shown in Table 15, the plant pathogen controlling effect and the herbicidal effect are confirmed by the above criteria according to the following method.

Ethaboxam is attached to the corn seeds in doses of 3, 30, and 300 g/100 kg of seeds. Next, a soil is packed in a pot, and the seeds and seeds of the weeds are sown. On the day of sowing, the PPO inhibitor is uniformly applied to the soil surface in doses of 25, 50, 100, 200, and 400 g/ha. The pot is placed in a greenhouse. On day 15 after the sowing, the plant pathogen controlling effect and the herbicidal effect are investigated.

TABLE 15

| Combination | Seed treatment compound | PPO inhibitor |
|---|---|---|
| 6-1 | Ethaboxam | Flumioxazin |
| 6-2 | Ethaboxam | Saflufenacil |
| 6-3 | Ethaboxam | Sulfentrazone |
| 6-4 | Ethaboxam | Oxyfluorfen |
| 6-5 | Ethaboxam | Fomesafen-sodium |
| 6-6 | Ethaboxam | Compound 1 |

Example 10

In the combinations shown in Table 16, the plant pathogen controlling effect and the herbicidal effect are confirmed by the above criteria according to the following method.

A soil is packed in a pot, and weeds are sown, then a PPO inhibitor is uniformly applied to the soil surface in doses of 25, 50, 100, 200, and 400 g/ha. After 7 days, the corn seeds to which ethaboxam is attached in doses of 3, 30, and 300 g/100 kg of seeds are sown. The pot is placed in a greenhouse. On day 15 after the sowing, the plant pathogen controlling effect and the herbicidal effect are investigated.

TABLE 16

| Combination | Seed treatment compound | PPO inhibitor |
|---|---|---|
| 7-1 | Ethaboxam | Flumioxazin |
| 7-2 | Ethaboxam | Saflufenacil |
| 7-3 | Ethaboxam | Sulfentrazone |
| 7-4 | Ethaboxam | Oxyfluorfen |
| 7-5 | Ethaboxam | Fomesafen-sodium |
| 7-6 | Ethaboxam | Compound 1 |

INDUSTRIAL APPLICABILITY

According to the method for controlling noxious organisms of the present invention, noxious organisms in a field of soybean, corn or cotton can be efficiently controlled.

What is claimed is:

1. A method for controlling weeds in a field of soybean, corn or cotton, wherein fomesafen-sodium is applied before, at or after sowing a soybean, corn or cotton seed treated with ethaboxam.

2. The control method according to claim 1, comprising the step of applying fomesafen-sodium to the field before sowing the soybean, corn or cotton seed.

3. The control method according to claim 1, comprising the step of applying fomesafen-sodium to the field at sowing the soybean, corn or cotton seed.

4. The control method according to claim 1, comprising the step of applying fomesafen-sodium to the field after sowing the soybean, corn or cotton seed.

5. A method for controlling weeds in a field of soybean, corn or cotton, which comprises the steps of
treating a soybean, corn or cotton seed with ethaboxam, and
applying fomesafen-sodium before, at or after sowing the soybean, corn or cotton seed treated with ethaboxam.

6. The control method according to claim 5, comprising the step of applying fomesafen-sodium to the field before sowing the soybean, corn or cotton seed.

7. The control method according to claim 5, comprising the step of applying fomesafen-sodium to the field at sowing the soybean, corn or cotton seed.

8. The control method according to claim 5, comprising the step of applying fomesafen-sodium to the field after sowing the soybean, corn or cotton seed.

* * * * *